United States Patent
Haas et al.

(10) Patent No.: US 6,596,881 B2
(45) Date of Patent: Jul. 22, 2003

(54) PROCESS FOR THE EPOXIDATION OF OLEFINS

(75) Inventors: Thomas Haas, Frankfurt (DE); Willi Hofen, Rodenbach (DE); Georg Thiele, Hanau (DE); Jörg Sauer, Mobile, AL (US)

(73) Assignees: Degussa AG, Düsseldorf (DE); Uhde GmbH, Dortmund (DE)

( * ) Notice: Subject to any disclaimer, the term of this patent is extended or adjusted under 35 U.S.C. 154(b) by 0 days.

(21) Appl. No.: 10/170,196

(22) Filed: Jun. 13, 2002

(65) Prior Publication Data

US 2003/0050488 A1 Mar. 13, 2003

Related U.S. Application Data

(60) Provisional application No. 60/297,534, filed on Jun. 13, 2001.

(51) Int. Cl.$^7$ .............................................. C07D 301/12
(52) U.S. Cl. ........................................ 549/531; 549/523
(58) Field of Search ................................. 549/531, 523

(56) References Cited

U.S. PATENT DOCUMENTS

| | | | |
|---|---|---|---|
| 2,870,171 A | 1/1959 | Gable | |
| 4,410,501 A | 10/1983 | Taramasso et al. | 423/326 |
| 4,833,260 A | 5/1989 | Neri et al. | |
| 5,523,426 A | 6/1996 | Jubin, Jr. et al. | |
| 5,591,875 A | 1/1997 | Chang et al. | |
| 5,599,955 A | 2/1997 | Vora et al. | |
| 5,620,935 A | 4/1997 | Thiele | |
| 5,675,026 A | 10/1997 | Thiele | |
| 5,760,253 A | 6/1998 | Danner et al. | |
| 5,849,937 A | 12/1998 | Jubin, Jr. et al. | |
| 5,849,938 A | 12/1998 | Reuter et al. | |
| 5,912,367 A | 6/1999 | Chang | 549/529 |
| 6,042,807 A | 3/2000 | Faraj | |
| 6,063,941 A | 5/2000 | Gilbeau | |
| 6,372,924 B2 | 4/2002 | Thiele | |

FOREIGN PATENT DOCUMENTS

| | | |
|---|---|---|
| DE | 196 23 611 | 12/1997 |
| DE | 197 23 950 | 12/1998 |
| DE | 197 54 185 | 2/1999 |
| DE | 198 35 907 | 2/2000 |
| EP | 0 100 118 | 2/1984 |
| EP | 0 100 119 | 2/1984 |
| EP | 0 106 671 | 4/1984 |
| EP | 0 230 349 | 7/1987 |
| EP | 0 230 949 | 8/1987 |
| EP | 0 568 336 | 11/1993 |
| EP | 0 568 337 | 11/1993 |
| EP | 0 583 828 | 2/1994 |
| EP | 0 645 473 | 3/1995 |
| EP | 0 659 473 | 6/1995 |
| EP | 0 712 852 | 5/1996 |
| EP | 0 719 768 | 7/1996 |
| EP | 0 757 045 | 2/1997 |
| EP | 0 795 537 | 9/1997 |
| EP | 0 827 765 | 3/1998 |
| EP | 0 930 308 | 7/1999 |
| EP | 0 936 219 | 8/1999 |
| EP | 1 066 711 | 12/1999 |
| EP | 1 138 387 | 10/2001 |
| JP | 2166636 | 6/1990 |
| WO | WO 97/47613 | 12/1997 |
| WO | WO 97/47614 | 12/1997 |
| WO | WO 99/01445 | 1/1999 |
| WO | WO 99/07690 | 2/1999 |
| WO | WP 99/11639 | 3/1999 |
| WO | WO 99/66696 | 12/1999 |
| WO | WO 00/07695 | 2/2000 |
| WO | WO 00/17178 | 3/2000 |

OTHER PUBLICATIONS

European Search Report issued for EP 01 10 5247 dated Jun. 8, 2001.

*Primary Examiner*—Ba K. Trinh
(74) *Attorney, Agent, or Firm*—Smith, Gambrell & Russell, LLP

(57) ABSTRACT

A process for the catalytic epoxidation of olefins with hydrogen peroxide in a continuous flow reaction system, wherein the reaction mixture is passed through a fixed catalyst bed in down-flow operation mode and the reaction heat is at least partially removed during the course of the reaction.

25 Claims, No Drawings

PROCESS FOR THE EPOXIDATION OF OLEFINS

REFERENCE TO RELATED APPLICATION

This application claims the benefit of provisional application No. 60/297,534 Jun. 13,2001 which is relied on and incorporated herein by reference.

INTRODUCTION AND BACKGROUND

The present invention relates to a process for the catalytic epoxidation of olefins with hydrogen peroxide in a continuous flow reaction system, wherein the reaction mixture is passed through a fixed catalyst bed.

From EP-A 100 119 it is known that propene can be converted by hydrogen peroxide into propene oxide if a titanium-containing zeolite is used as catalyst.

Unreacted hydrogen peroxide cannot be recovered economically from the epoxidation reaction mixture. Furthermore, unreacted hydrogen peroxide involves additional effort and expenditure in the recovery of the reaction mixture. The epoxidation of propene is therefore preferably carried out with an excess of propene and up to a high hydrogen peroxide conversion. In order to achieve a high hydrogen peroxide conversion it is advantageous to use a continuous flow reaction system. Such a reaction system may comprise either one or more tubular flow reactors or an arrangement of two or more flow mixing reactors connected in series. Examples of flow mixing reactors are stirred tank reactors, recycle reactors, fluidized bed reactors and fixed bed reactors with recycling of the liquid phase.

In order to achieve a high reaction rate a high propene concentration in the liquid phase is necessary. The reaction is therefore preferably carried out under a propene atmosphere at elevated pressure with the effect that a multiphase reaction system is in general present.

Furthermore the epoxidation of olefins with hydroperoxides is like most oxidation reactions highly exothermic. Thus precautions have to be taken to ensure sufficient removal of the heat generated by the exothermic reaction in order to control the reaction. This problem is especially pronounced in continues flow systems using fixed bed reactors. Moreover conversion and product selectivity in epoxidation reactions of olefins are highly susceptible to temperature changes with the effect that efficient temperature control is off uppermost importance.

In the publication by A. Gianetto, "Multiphase Reactors: Types, Characteristics and Uses", in Multiphase Chemical Reactors: Theory, Design, Scale-up, Hemisphere Publishing Corporation, 1986 criteria governing the choice between up-flow and down-flow fixed bed multiphase reactors are given. Advantages of up-flow regime compared to down-flow regime are:

- better mixing resulting in improved heat and mass transfer;
- at the same fluid flow rates the up-flow operation provides higher volumetric gas/liquid mass transfer coefficients;
- better liquid distribution in the cross section;
- better heat dissipation and more uniform temperature;
- better wetting of the catalyst and therefore increased catalyst effectiveness;
- slower aging of the catalyst
- avoiding compacting of the catalyst bed.

Disadvantages are:
- larger pressure drops and higher energy expenditure for pumping;
- reactor has to comprise means to hold the catalyst in place in case of high velocities;
- higher mass transfer resistance inside the liquid and an increase in possible homogeneous side reactions can occur.

In view of the advantages with respect to heat transfer and dissipation, up-flow operation of a fixed bed reactor for multiphase reaction systems is the natural choice for highly exothermic reactions where temperature control is important.

This is also reflected in WO 97/47614 where in example 8 reaction of propene with hydrogen peroxide using a fixed bed tubular reactor having a cooling jacket in up-flow operation is described. But nevertheless yield and product selectivity are still insufficient for commercial purposes.

EP-A 659 473 describes an epoxidation process wherein a liquid mixture of hydrogen peroxide, solvent and propene is led over a succession of fixed bed reaction zones connected in series in down-flow operation. No temperature control means are present within the reactor to remove the generated heat from the single reaction zones. Thus each reaction zone can be considered as an independent adiabatic reactor. In each reaction zone the reaction is performed to a partial conversion, the liquid reaction mixture is removed from each reaction zone, is led over an external heat exchanger to extract the heat of reaction, and the major proportion of this liquid phase is then recycled to this reaction zone and a minor proportion of the liquid phase is passed to the next zone. At the same time gaseous propene is fed in together with the liquid feed stock mixture, is guided in a parallel stream to the liquid phase over the fixed bed reaction zones, and is extracted at the end of the reaction system in addition to the liquid reaction mixture as an oxygen-containing waste gas stream. Although this reaction procedure enables the propene oxide yield to be raised compared to conventional tubular reactors without the temperature control described in EP-A 659 473, it nevertheless involves considerable additional costs on account of the complexity of the reaction system required to carry out the process.

From U.S. Pat. No. 5,849,937 a process for epoxidation of propene using hydroperoxides especially organic hydroperoxides is known. The reaction mixture is fed to a cascade of serially connected fixed bed reactors in down-flow regime with respect to each single reactor. Similarly to the teaching of EP-A 659 473 in each reactor only partial conversion is accomplished and the reactors are not equipped with heat exchange means. Like in EP-A 659 473 the reaction heat is removed by passing the effluent from each reactor through heat exchangers prior to introducing the reaction mixture to the next fixed bed reactor in series thereby adding to the complexity of the reaction system.

The disadvantages of the reaction systems as discussed in EP-A 659 473 and U.S. Pat. No. 5,849,937 are the complexity and thus the increased costs for investment and the high susceptibility to changes of process parameters like flow velocity due to the adiabaticly operated independent reaction zones and reactors respectively.

In view of the cited prior art it is therefore an object of the present invention to provide a process for the epoxidation of olefins that results in improved conversion and product selectivity compared to WO 97/47614 while avoiding the disadvantages of the teachings of EP-A 659 473 and U.S. Pat. No. 5,849,937 which can be carried out using conventional reaction systems.

SUMMARY OF THE INVENTION

The above and other objects of the invention can be achieved by a process for the catalytic epoxidation of olefins with hydrogen peroxide in a continuous flow reaction system, wherein the reaction mixture is passed through a fixed catalyst bed in down-flow operation mode and the reaction heat is at least partially removed during the course of the reaction. The process of the present invention is therefore preferably conducted in a fixed bed reactor comprising cooling means.

A particularly preferred embodiment of the present invention refers to a process for the catalytic epoxidation of propene with hydrogen peroxide in a continuous flow reaction system conducted in a multiphase reaction mixture comprising an liquid aqueous hydrogen peroxide rich phase containing methanol and an liquid organic propene rich phase, wherein the reaction mixture is passed through a fixed catalyst bed in down-flow operation mode and the reaction heat is at least partially removed during the course of the reaction.

The present inventors have surprisingly discovered, contrary to the general textbook knowledge as exemplified by A. Gianetto supra, that a cooled fixed bed reactor can be successfully operated in a down-flow operation to increase product selectivity and thereby overall product yield compared to an up-flow operation as previously used in the prior art. This effect is even more surprising since it is known that the epoxidation of olefin is a highly exothermic reaction that is difficult to control since this reaction has a considerably high activation temperature and therefore has to be conducted at a certain minimum temperature to achieve economically reasonable conversion. But on the other hand the heat generated by the exothermic reaction has to be effectively removed from the reactor since at increased temperatures unwanted side reactions take place with the result that product selectivity is decreased. The effect of limited temperature increase within the catalyst bed is discussed to some extent in EP-A-659 473. With respect to the examples it is disclosed that in conventional tubular reactors temperature rise in the catalyst bed exceeds 15° C. whereas according to the examples in EP-A-659 473 the temperature rise is 8° C. at the most and in the preferred embodiment 5½° C. Thus according to the teaching of EP-A-659 473 temperature rise within the catalyst bed has to be kept as low as possible in order to achieve high yields of propylene oxide. This reduced temperature rise could only be achieved according to EP-A-659 473 by conducting the reaction in a single reaction zone to only a partial conversion with the result that the majority of the reaction mixture has to be recycled, and by intermediately cooling the reaction mixture.

According to the teaching of A. Gianetto et al. when operating a conventional tubular fixed bed reactor poor heat dissipation and nonuniform temperature within the catalyst bed has to be expected in case of downflow operation mode. Thus it has to be expected that by using a downflow operation mode in a conventional cooled fixed bed reactor without intermediate external cooling of the reaction mixture a high temperature rise within the catalyst bed due to poor heat dissipation would occur that should dramatically decrease product selectivity and thus the yield. But contrary to this expectation, as will be shown in more detail below in the examples, better product selectivity at the same conversion compared to up-flow operation mode is achieved and similar or even better overall yields based on hydrogen peroxide compared to the most preferred embodiments in EP-A-659 473 are obtainable although a conventional reactor system without intermediate external cooling was used.

DETAILED DESCRIPTION OF THE INVENTION

In the practice of the present invention any reactor having a fixed catalyst bed and cooling means can be used. Adiabatic reaction conditions as taught in EP-A 659 473 and U.S. Pat. No. 5,849,937 should be avoided. Preferably, tubular, multi-tubular or multi-plate reactors are used. Most preferably, tubular reactors having a cooling jacket are applied since they are standardly available at relatively low cost. As cooling medium that is pumped through the cooling means, preferably the cooling jacket, all standard cooling media like oils, alcohols, liquid salts or water can be used. Water is most preferred.

The process according to the invention for the epoxidation of olefins, preferably propene, is typically carried out at a temperature of 30° to 80° C., preferably at 40° to 60° C. According to a preferred embodiment of the present invention the temperature profile within the reactor is maintained such that the cooling medium temperature of the cooling means of the tubular reactor is at least 40° C. and the maximum temperature within the catalyst bed is 60° C. at the most, preferably 55° C. By preference the temperature of the cooling medium is controlled by a thermostat.

The maximum temperature within the catalyst bed is measured with a plurality of suitable temperature measurement means like thermocouples or a Pt-100 arranged approximately along the axis of the preferably tubular reactor in suitable distances with respect to each other. Whereby number, position within the reactor and distances between the temperature measurement means are adjusted to measure the temperature of the catalyst bed within the entire reactor as exact as necessary.

The maximum temperature of the catalyst bed can be adjusted by different means. Depending on the selected reactor type the maximum temperature of the catalyst bed can be adjusted by controlling the flow rate of the reaction mixture passing through the reactor, by controlling the flow rate of the cooling medium passing through the cooling means or by lowering the catalyst activity, for instance by diluting the catalyst with inert material.

The flow rate of the cooling medium is preferably adjusted to keep the temperature difference between entry of the cooling medium into the cooling means and exit below 5° C., preferably below 3° C., most preferably 2° C.

By selecting such a narrowly defined temperature profile within the reactor an optimized balance between hydrogen peroxide conversion and olefin oxide selectivity can be achieved.

The pressure within the reactor is usually maintained at 5 to 50 bar preferably 15 to 30 bar.

According to a preferred embodiment the reaction mixture is passed through the catalyst bed with a superficial velocity from 1 to 100 m/h, preferably 5 to 50 m/h, most preferred 5 to 30 m/h. The superficial velocity is defined as the ratio of volume flow rate/cross section of the catalyst bed. Consequently the superficial velocity can be varied in a given reactor by adjusting the flow rate of the reaction mixture.

Additionally it is preferred to pass the reaction mixture through the catalyst bed with a liquid hourly space velocity (LHSV) from 1 to 20 $h^{-1}$, preferably 1.3 to 15 $h^{-1}$.

Whenever the flow rate of the reaction mixture is adjusted to fulfill the above defined requirements for superficial velocity and liquid hourly space velocity particularly high selectivities can be achieved.

According to particularly preferred embodiment of the present invention the process is conducted to maintain the catalyst bed in a trickle bed state. It has been surprisingly discovered that if the trickle bed state is maintained under certain flow conditions the effect of the present invention i.e. the increased propene oxide selectivity will be particularly pronounced.

These conditions are as follows:

$$G/\lambda < 2000 \ m/h \text{ and}$$

$$L\psi < 50 \ m/h,$$

wherein

G is the gaseous superficial velocity defined as the gaseous flow rate in m³/h in the continuous flow reactor divided by the cross-section of the catalyst bed in m², L is the liquid superficial velocity defined as the liquid flow rate in m³/h in the continuous flow reactor divided by the cross-section of the catalyst bed in m², $$\lambda = \left[\left(\frac{\rho_G}{\rho_W}\right)\left(\frac{\rho_L}{\rho_{Air}}\right)\right]^{1/2},$$

and $$\psi = \left(\frac{\sigma_W}{\sigma_L}\right) \cdot \left[\left(\frac{\mu_L}{\mu_W}\right)\left(\frac{\rho_W}{\rho_L}\right)^2\right]^{1/3}$$

$\rho_G$ is the density of the gaseous phase in g/cm³,
$\rho_L$ is the density of the liquid phase in g/cm³,
$\rho_W$ is the density of water in g/cm³,
$\rho_{Air}$ is the density of air in g/cm³,
$\sigma_W$ is the surface tension of water in dyn/cm,
$\sigma_L$ is the surface tension of the liquid phase in dyn/cm,
$\mu_L$ is the viscosity of the liquid phase in centipoise,
$\mu_W$ is the viscosity of water in centipoise.

In order to be able to operate the process continuously when changing and/or regenerating the epoxidation catalyst, two or more flow reactors may if desired also be operated in parallel or in series in the before-described manner.

Crystalline, titanium-containing zeolites especially those of the composition $(TiO_2)_x(SiO_2)_{1-x}$ where x is from 0.001 to 0.05 and having a MFI or MEL crystalline structure, known as titanium silicalite-1 and titanium silicalite-2, are suitable as catalysts for the epoxidation process according to the invention. Such catalysts may be produced for example according to the process described in U.S. Pat. No. 4,410,501. The titanium silicalite catalyst may be employed as a shaped catalyst in the form of granules, extrudates or shaped bodies. For the forming process the catalyst may contain 1 to 99% of a binder or carrier material, all binders and carrier materials being suitable that do not react with hydrogen peroxide or with the epoxide under the reaction conditions employed for the epoxidation. Extrudates with a diameter of 1 to 5 mm are preferably used as fixed bed catalysts.

When practicing the present invention it is preferred that the overall feed stream to the reactor comprises an aqueous hydrogen peroxide solution, an olefin and an organic solvent. Thereby these components may be introduced into the reactor as independent feeds or one or more of these feeds are mixed prior to introduction into the reactor.

Using the process according to the invention any olefins can be epoxidized in particular olefins with 2 to 6 carbon atoms. The process according to the invention is most particularly suitable for the epoxidation of propene to propene oxide. For economic reasons it would be preferred for an industrial scale process to use propene not in a pure form but as a technical mixture with propane that as a rule contains 1 to 15 vol. % of propane. Propene may be fed as a liquid as well as in gaseous form into the reaction system.

The hydrogen peroxide is used in the process according to the invention in the form of an aqueous solution with a hydrogen peroxide content of 1 to 90 wt. %, preferably 10 to 70 wt. % and particularly preferably 30 to 50 wt. %. The hydrogen peroxide may be used in the form of the commercially available, stabilized solutions. Also suitable are unstabilized, aqueous hydrogen peroxide solutions such as are obtained in the anthraquinone process for producing hydrogen peroxide.

The reaction is preferably carried out in the presence of a solvent in order to increase the solubility of the olefin, preferably propene, in the liquid phase. Suitable as solvent are all solvents that are not oxidized or are oxidized only to a slight extent by hydrogen peroxide under the chosen reaction conditions, and that dissolve in an amount of more than 10 wt. % in water. Preferred are solvents that are completely miscible with water. Suitable solvents include alcohols such as methanol, ethanol or tert.-butanol; glycols such as for example ethylene glycol, 1,2-propanediol or 1,3-propanediol; cyclic ethers such as for example tetrahydrofuran, dioxane or propylene oxide; glycol ethers such as for example ethylene glycol monomethyl ether, ethylene glycol monoethyl ether, ethylene glycol monobutyl ether or propylene glycol monomethyl ether, and ketones such as for example acetone or 2-butanone. Methanol is particularly preferably used as solvent.

The olefin is preferably employed in excess relative to the hydrogen peroxide in order to achieve a significant consumption of hydrogen peroxide, the molar ratio of olefin, preferably propene, to hydrogen peroxide preferably being chosen in the range from 1.1 to 30. The solvent is preferably added in a weight ratio of 0.5 to 20 relative to the amount of hydrogen peroxide solution used. The amount of catalyst employed may be varied within wide limits and is preferably chosen so that a hydrogen peroxide consumption of more than 90%, preferably more than 95%, is achieved within 1 minute to 5 hours under the employed reaction conditions.

According to one embodiment of the present invention reaction conditions like temperature, pressure, selection of olefin and selection of solvent and relative amounts of the components of the reaction mixture are chosen to ensure the presence of only one aqueous liquid phase wherein the olefin is dissolved. An additional gaseous olefin containing phase may also be present.

But it is preferred to conduct the epoxidation of olefins with hydrogen peroxide in a multiphase reaction mixture comprising a liquid aqueous hydrogen peroxide rich phase containing an organic solvent having a solubility in water of at least 10% by weight at 25° C. and a liquid organic olefin rich phase. Thereby an even better product selectivity can be achieved.

As will be appreciated by any person skilled in the art the presence of two immiscible liquid phases in a reaction system comprising an olefin, an water miscible organic solvent and an aqueous hydrogen peroxide solution will depend on many different factors. First of all the presence of an additional olefin rich liquid organic phase will depend on the temperature and pressure applied in the reactor and the selected olefin. Preferably the applied pressure is at or above the vapor pressure of the olefin at the chosen temperature. Furthermore it will depend on the selection of the organic solvent. Suitable as organic solvent are all solvents that dissolve in an amount of more than 10 wt. % in water at 25° C. Preferred are solvents that dissolve in an amount of more than 30 wt. % in water at 25° C. preferably more than 50 wt. % in water at 25° C. The most preferred solvents are completely miscible with water. In principle all solvents as exemplified above can also be used in this preferred embodiment as long as the conditions are met to ensure the presence of two liquid phases.

Additionally the presence of a second organic olefin rich phase will depend on the relative amounts of olefin, water and solvent. The amount of solvent is chosen to achieve sufficient solubility of the olefin in the hydrogen peroxide rich aqueous phase in order to get the desired rate of reaction. At a given temperature, pressure, olefin and solvent the relative amounts of ingredients can be adjusted to ensure formation of a second liquid organic phase. That is, to ensure the formation of a second liquid organic olefin rich phase the amount of olefin has to be selected in excess of the amount soluble in the aqueous phase at the chosen temperature and pressure.

A simple means of experimentally confirming the presence of a second liquid organic phase at the reaction conditions is by collecting a sample of the reaction mixture in a container equipped with a sight glass at the temperature and pressure used in the process. Alternatively, the reactor may be equipped with a sight glass at a suitable position to observe the phase boundary directly during the reaction. In case of a continuous flow reactor the sight glass is preferably positioned near the outlet of the reactor effluent to have an optimal control that two liquid phases are present through out the entire residence time within the reactor.

Thus a person skilled in the art can without any effort verify whether when applying certain selections for olefins, solvents and reaction parameters a two-liquid phase system as required by the present invention is present and can adjust by variation of the parameters as discussed above in detail the reaction system in order to establish a second liquid organic phase.

According to a most preferred embodiment of the present invention the olefin is selected to be propene, and methanol is used as a solvent. For example for a reaction mixture comprising propene, methanol, and aqueous hydrogen peroxide at a reaction temperature between 30° C. and 80° C., a pressure from 5 to 50 bar the ratio of propene flow to total flow in case of a continuous flow system can be adjusted to be in the range of 0.1 to 1, preferably 0.2 to 1 in order to obtain a second liquid organic phase.

An additional gas phase comprising olefin vapor and optionally an inert gas i.e. a gas that does not interfere with the epoxidation can be additionally present according to the present invention. Adding an inert gas is useful to maintain a constant pressure inside the reactor and to remove oxygen gas formed by the decomposition of a small part of the hydrogen peroxide charged to the reactor.

The present invention refers to a process for the catalytic epoxidation of olefins with hydrogen peroxide in a continuous flow reaction system, wherein the reaction mixture is passed through a fixed catalyst bed in down-flow operation mode and the reaction heat is at least partially removed during the course of the reaction.

Preferred conditions for the present invention include:
a) a fixed bed reactor comprising cooling means is used;
b) the fixed bed reactor is a tubular reactor and the cooling means is a cooling jacket;
c) the reaction mixture is passed through the catalyst bed with a superficial velocity from 1 to 100 m/h, preferably 5 to 50 m/h, most preferably 5 to 30 m/h; and
d) the reaction mixture is passed through the catalyst bed with a liquid hourly space velocity (LHSV) from 1 to 20 h$^{-1}$, preferably 1.3 to 15 h$^{-1}$.

According to a preferred embodiment, the fixed catalyst bed is maintained in a trickle bed state.

Preferably trickle bed state is maintained under following flow conditions:

$$G/\lambda < 2000 \; m/h \text{ and}$$

$$L\psi < 50 \; m/h,$$

wherein
G is the gaseous superficial velocity defined as the gaseous flow rate in m$^3$/h in the continuous flow reaction system divided by the cross-section of the catalyst bed in m$^2$,
L is the liquid superficial velocity defined as the liquid flow rate in m$^3$/h in the continuous flow reaction system divided by the cross-section of the catalyst bed in m$^2$, $$\lambda = \left[\left(\frac{\rho_G}{\rho_W}\right)\left(\frac{\rho_L}{\rho_{Air}}\right)\right]^{1/2},$$

and $$\psi = \left(\frac{\sigma_W}{\sigma_L}\right) \cdot \left[\left(\frac{\mu_L}{\mu_W}\right)\left(\frac{\rho_W}{\rho_L}\right)^2\right]^{1/3}$$

$\rho_G$ is the density of the gaseous phase in g/cm$^3$,
$\rho_L$ is the density of the liquid phase in g/cm$^3$,
$\rho W$ is the density of water in g/cm$^3$,
$\rho_{Air}$ is the density of air in g/cm$^3$,
$\sigma_W$ is the surface tension of water in dyn/cm,
$\sigma_L$ is the surface tension of the liquid phase in dyn/cm,
$\mu_L$ is the viscosity of the liquid phase in centipoise,
$\mu_W$ is the viscosity of water in centipoise.

The reaction temperature is preferably from 30 to 80° C., preferably from 40 to 60° C.

A temperature profile within the reactor is preferably maintained such that the cooling medium temperature of the cooling means is at least 40° C. and the maximum temperature within the catalyst bed is 60° C. at the most.

Other preferred operating conditions of the present invention are:
the pressure within the reactor is maintained at 5 to 50 bar, more preferably at 15 to 30 bar;
the overall feed stream to the reactor comprises an aqueous hydrogen peroxide solution, an olefin and an organic solvent;
the reaction is conducted in a multiphase reaction mixture comprising an liquid aqueous hydrogen peroxide rich phase containing an organic solvent having a solubility in water of at least 10% by weight at 25° C. and an liquid organic olefin rich phase;
the organic solvent is methanol;
a titanium-containing zeolite is used as catalyst; and
the olefin is propene.

In a preferred embodiment the present invention refers to a process for the catalytic epoxidation of propene with hydrogen peroxide in a continuous flow reaction system conducted in a multiphase reaction mixture comprising an liquid aqueous hydrogen peroxide rich phase containing methanol and an liquid organic propene rich phase, wherein the reaction mixture is passed through a fixed catalyst bed in down-flow operation mode and the reaction heat is at least partially removed during the course of the reaction.

The present invention will be explained in more detail referring to the following examples:

EXAMPLES 1 and 2 and COMPARATIVE EXAMPLES 1-4

A titanium-silicate catalyst was employed in all examples. The titanium-silicate powder was shaped into 2 mm extrudates using a silica sol as binder in accordance with example 5 in EP 00 106 671.1 which is relied on and incorporated herein by reference. The $H_2O_2$ employed was prepared according to the anthraquinone process as a 40 wt-% aqueous solution.

Epoxidation is carried out continuously in a reaction tube of 300 ml volume, a diameter of 10 mm and a length of 4 m. The equipment is furthermore comprised of three containers for liquids and relevant pumps and a liquid separating vessel. The three containers for liquids comprised methanol, the 40% $H_2O_2$ and propene. The 40% $H_2O_2$ was adjusted with ammonia to a pH of 4.5. The reaction temperature is controlled via an aqueous cooling liquid circulating in a cooling jacket whereby the cooling liquid temperature is controlled by a thermostat. The reactor pressure was 25 bar absolute. Mass flow of the feeding pumps was adjusted to result in a propene feed concentration of 21.5 wt-%, a methanol feed concentration of 57 wt-% and an $H_2O_2$ feed concentration of 9.4 wt-%.

When performing the examples and comparative examples flow mode (downflow (DF) mode or upflow (UF) mode) as well as the cooling jacket temperature and the total mass flow were varied as indicated in Table 1. The flow rate was adjusted to achieve comparable conversions. The product stream was analyzed by gas chromatography and the $H_2O_2$ conversion was determined by titration. Propene selectivity was calculated as the ratio of the amount of propene oxide relative to the total amount of propene oxide and oxygen containing hydrocarbons formed during the epoxidation reaction such as 1-methoxy-2-propanol, 2-methoxy-1-propanol and 1,2-propanediol.

TABLE 1

| No. | Mode | Cooling Jacket Temperature ° C. | Flow Rate kg/h | $H_2O_2$ Conversion [%] | Propene Oxide Selectivity [%] | Propene Oxide Yield based on $H_2O_2$ [%] |
|---|---|---|---|---|---|---|
| CE1 | UF | 30 | 0.35 | 81 | 95 | 77 |
| CE2 | UF | 40 | 0.55 | 96 | 93 | 89 |
| CE3 | UF | 60 | 1.8 | 92 | 85 | 78 |
| CE4 | UF | 80 | 4.1 | 87 | 70 | 61 |
| E1 | DF | 40 | 0.35 | 96 | 96 | 92 |
| E2 | DF | 40 | 0.7 | 81 | 98 | 79 |

UF = up-flow mode
DF = down-flow mode

When comparing CE1 and CE2 with CE3 and CE4 it is evident that product selectivity strongly depends on the reaction temperature with decreasing selectivity with increasing temperature. Thus good heat dissipation and uniform temperature is important. In this respect a person skilled in the art would prefer the up-flow mode. Surprisingly, as can be seen from comparing E1 and CE2 the results in down-flow mode are even better at the same reaction temperature.

Further variations and modification of the foregoing will be apparent to those skilled in the art and are intended to be encompassed by the claims appended hereto.

We claim:

1. A process for the catalytic epoxidation reaction of an olefin with hydrogen peroxide in a continuous flow reaction system, comprising passing a reaction mixture containing an olefin and hydrogen peroxide through a fixed catalyst bed in down-flow operation mode for an epoxidation reaction and at least partially removing the reaction heat created during the course of the reaction.

2. The process of claim 1, wherein a fixed bed reactor comprising cooling means is used.

3. The process of claim 2, wherein the fixed bed reactor is a tubular reactor and the cooling means is a cooling jacket.

4. The process of claim 1, wherein the reaction mixture is passed through the catalyst bed with a superficial velocity from 1 to 100 m/h.

5. The process of claim 1, wherein the reaction mixture is passed through the catalyst bed with a superficial velocity from 5 to 50 m/h.

6. The process of claim 1, wherein the reaction mixture is passed through the catalyst bed with a superficial velocity from 5 to 30 m/h.

7. The process of claim 1, wherein the reaction mixture is passed through the catalyst bed with a liquid hourly space velocity (LHSV) from 1 to 20 $h^1$.

8. The process of claim 1, wherein the reaction mixture is passed through the catalyst bed with a liquid hourly space velocity (LHSV) from 1.3 to 15 $h^1$.

9. The process of claim 1, wherein the fixed catalyst bed is maintained in a trickle bed state.

10. The process of claim 9, wherein trickle bed state is maintained under the following flow conditions:

$$G/\lambda < 2000 \ m/h \text{ and}$$

$$L\psi < 50 \ m/h,$$

wherein

G is the gaseous superficial velocity defined as the gaseous flow rate in $m^3/h$ in the continuous flow reactor divided by the cross-section of the catalyst bed in $m^2$, L is the liquid superficial velocity defined as the liquid flow rate in $m^3/h$ in the continuous flow reactor divided by the cross-section of the catalyst bed in $m^2$, $$\lambda = \left[\left(\frac{\rho_G}{\rho_W}\right)\left(\frac{\rho_L}{\rho_{Air}}\right)\right]^{1/2},$$

and $$\psi = \left(\frac{\sigma_W}{\sigma_L}\right) \cdot \left[\left(\frac{\mu_L}{\mu_W}\right)\left(\frac{\rho_W}{\rho_L}\right)^2\right]^{1/3}$$

$\rho_G$ is the density of the gaseous phase in $g/cm^3$,
$\rho_L$ is the density of the liquid phase in $g/cm^3$,
$\rho_W$ is the density of water in $g/cm^3$,
$\rho_{Air}$ is the density of air in $g/cm^3$,
$\sigma_W$ is the surface tension of water in dyn/cm,
$\sigma_L$ is the surface tension of the liquid phase in dyn/cm,
$\mu_L$ is the viscosity of the liquid phase in centipoise,
$\mu_W$ is the viscosity of water in centipoise.

11. The process of claim 1, wherein the reaction is carried out at a temperature from 30 to 80° C.

12. The process of claim 1, wherein the reaction is carried out at a temperature from 40 to 60° C.

13. The process of claim 12, wherein a temperature profile within the reactor is maintained such that the cooling medium temperature of the cooling means is at least 40° C. and the maximum temperature within the catalyst bed is 60° C. at the most.

14. The process of claim 1, wherein the pressure within the reactor is maintained at 5 to 50 bar.

15. The process of claim 1, wherein the pressure within the reactor is maintained at 15 to 30 bar.

16. The process of claim 1, wherein a feed stream is conveyed to the reactor which comprises an aqueous hydrogen peroxide solution, an olefin and an organic solvent as the overall feed stream.

17. The process of claim 1, wherein the reaction is conducted in a multiphase reaction mixture comprising a liquid aqueous hydrogen peroxide rich phase containing an organic solvent having a solubility in water of at least 10% by weight at 25° C. and a liquid organic olefin rich phase.

18. The process of claim 1 wherein separate feed streams of hydrogen peroxide, olefin and organic solvent are conveyed to the reactor.

19. The process of claim 17, wherein the organic solvent is methanol.

20. The process of claim 18, wherein the organic solvent is methanol.

21. The process of claim 1, wherein a titanium-containing zeolite is the catalyst.

22. The process of claim 1, wherein the olefin is propene.

23. A process for the catalytic epoxidation of propene with hydrogen peroxide in a continuous flow reaction system comprising forming a multiphase reaction mixture of a liquid aqueous hydrogen peroxide rich phase containing methanol and a liquid organic propene rich phase, passing the reaction mixture through a fixed catalyst bed in down-flow operation mode and at least partially removing reaction heat during the course of the reaction.

24. The process of claim 16, wherein the reaction is conducted in a multiphase reaction mixture comprising a liquid aqueous hydrogen peroxide rich phase containing an organic solvent having a solubility in water of at least 10% by weight at 25° C. and a liquid organic olefin rich phase.

25. The process of claim 16 wherein at least two of the components of the reaction mixture are mixed together prior to introducing them into the reactor.

* * * * *